United States Patent [19]
Shinitzky et al.

[11] Patent Number: 5,912,250
[45] Date of Patent: *Jun. 15, 1999

[54] USE OF IMMUNOSUPPRESSIVE AGENTS FOR THE TREATMENT OF SCHIZOPHRENIA

[75] Inventors: Meir Shinitzky, Kfar Shmaryahu, Israel; Michael Deckmann, Guebwiller, France

[73] Assignee: Yeda Research and Development Co., Ltd., Rehovot, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,169

[22] PCT Filed: Jun. 13, 1995

[86] PCT No.: PCT/EP95/02289

§ 371 Date: Jan. 13, 1997

§ 102(e) Date: Jan. 13, 1997

[87] PCT Pub. No.: WO95/34306

PCT Pub. Date: Dec. 21, 1995

[30] Foreign Application Priority Data

Jun. 13, 1994 [IL] Israel ........................................ 110011

[51] Int. Cl.$^6$ ................................................. A61K 31/505
[52] U.S. Cl. ............................................................. 514/258
[58] Field of Search ............................................. 514/258

[56] References Cited

FOREIGN PATENT DOCUMENTS

WO 93/16727   9/1993   WIPO .

OTHER PUBLICATIONS

Shinitzky, Meir, et al., "Platelet Autoantibodies in Dementia and Schizophrenia, Possible Implication for Mental Disorders". *Ann. N.Y. Academy Sciences*, 1991; 621, pp. 205–217.

DeLisi, Lynn E., et al., "Are there Antibodies Against Brain in Sera from Schizophrenia Patients? Review and Prospectus," *Biol. Psychiatry*, 1985, 20:94–119; pp. 110–115.

Jankovic, B.D., "From Immunoneurology to Immunopsychiatry: Neuromodulating Activity of Anti–Brain Antibodies," *International Review of Neurobiology*, 1984, vol. 26, pp. 249–315.

Knight, John G., "Is Schizophrenia an Autoimmune Disease?—A Review," *Meth. and Find. Exptl. Clin. Pharmacol*, 1984; 6(7), pp. 395–403.

Teplizki, H. Amital, et al., "Autoantibodies to Brain and Polynucleotides in Patients with Schizophrenia: A Puzzle," *Immunol. Res.* 1992; 11, pp. 66–73.

Kessler, A., et al., "Platelets from Schizophrenia Patients Bear Autoimmune Antibodies that Inhibit Dopamine Uptake," *Psychobiology*, 1993, 21 (4), pp. 299–306.

(List continued on next page.)

*Primary Examiner*—Raymond Henley, III
*Attorney, Agent, or Firm*—Oliff & Berridge, PLC

[57] ABSTRACT

A pharmaceutical composition for the treatment of schizophrenic disorders that comprises a pharmaceutically acceptable carrier and as active ingredient an immunosuppressive agent.

14 Claims, 5 Drawing Sheets

OTHER PUBLICATIONS

Abramsky, O., et al., "Autoimmune Response to Dopamine–Receptor as a Possible Mechanism in the Pathogenesis of Parkinson's Disease and Schizophrenia," *Perspectives in Biology and Medicine*, 1978, pp. 104–114.

Leporrier, M., et al., "Detection and Quantification of Platelet–bound Antibodies with Immunoperoxidase," *British Journal of Haematology*, 1979, 42, pp. 605–611.

Ghadirian, A. M., "Some Recent Advances in the Study and Treatment of Schizophrenia in the Soviet Union," *The Psychiatric Journal of the University of Ottawa*, vol. II No. 3, pp. 112–116 (1980).

Levine, J., et al., "Treatment of Schizophrenia with an Immunosuppressant," *The Lancet*, vol. 344, Jul. 2, 1994, (8914) pp. 59–60.

Price, John, et al., "A Case of Cerebral Systemic Lupus Erythematosus Treated with Methylprednisolone Pulse Therapy," *Australian and New Zealand Journal of Psychiatry*, (1985) 19, pp. 184–194.

Valbonesi, M., et. al., "Plasma Exchange in Neurological Diseases, A Critical Approach," *Vox Sang*, 1983, 44, pp. 65–80.

Kay, S. R., et al., "The Positive and Negative Syndrome Scale (PANSS): Rationale and Standardisation," *British Journal of Psychiatry* (1989), 155 (suppl. 7), pp. 59–65.

Kay, Stanley R., et al., "The Positive and Negative Syndrome Scale—Spanish Adaptation," *The Journal of Nervous and Mental Disease*, vol. 178, No. 8, pp. 510–517 (1982).

Budavari, S. (ED.), *The Merck Index*, 1989, Merck & Co., Inc., 11th Ed., Rahway, NJ, p. 431 and p. 1224.

Ghadirian, Psychiatr. J. Univ. Ottawa, 2/3, pp. 112–116, 1977.

Martindale The Extra Pharmacopoeia, 28th ed. pp. 190–191, 1982.

USE OF IMMUNOSUPPRESSIVE AGENTS FOR THE TREATMENT OF SCHIZOPHRENIA

This application is a 371 of PCT/EP95/02289 filed Jun. 13, 1995.

FIELD AND BACKGROUND OF THE INVENTION

The present invention relates to the use of immunosuppressive agents for the treatment of schizophrenic disorders.

The schizophrenic disorders, as defined by DSM-III (the American Psychiatric Association's Diagnostic and Statistical Manual, 3rd edition) are mental disorders with a tendency towards chronicity which impairs functioning and which is characterized by psychotic symptoms involving disturbances of thinking, feeling and behavior.

Schizophrenia occurs worldwide. Although it is one of the most severe and prevalent mental disorders of well documented symptomatology and has been extensively investigated over the past decades, the etiology of this disease is still an enigma. Schizophrenic patients are mainly treated by chemotherapy with antipsychotic drugs, such as the neuroleptic drugs haloperidol and chlorpromazine. Electroconvulsive therapy is also used in some cases. However, individual response to each drug varies, and both chemotherapy and electroconvulsive therapy are not successful for many schizophrenic patients.

A series of biochemical findings have suggested that autoimmune elements might be implicated in the etiology of schizophrenia[1-6]. We recently detected autoimmune antibodies on platelets from schizophrenic patients which block dopamine uptake and cross-react with brain tissue[4,6]. In line with the hypothesis that autoimmune reaction against the dopamine receptor takes place in schizophrenia[7]$_1$, we have further suggested that the onset of the schizophrenia may stem from binding of platelet autoantibodies to one of the dopamine receptors in the central nervous system (CNS)[4,6]. However, the assumption that schizophrenia is an autoimmune disease has not been definitely ascertained as yet.

SUMMARY OF INVENTION

It has now been found in accordance with the present invention that mental patients with severe chronic schizophrenia, who did not respond to conventional treatments, may be successfully treated with azathioprine, a drug commonly used for autoimmune and inflammatory diseases. Treatment of patients has resulted in a remarkable improvement in the psychiatric state which correlated with a marked reduction in platelet-associated autoantibodies (PAA)

The present invention thus relates to pharmaceutical compositions for the treatment of schizophrenic disorders comprising as active ingredient an immunosuppressive agent together with a pharmaceutically acceptable carrier.

The invention further relates to the use of an immunosuppressive agent for the manufacture of pharmaceutical compositions for the treatment of schizophrenic disorders.

In another embodiment the invention relates to a method of treatment of a schizophrenic patient which comprises administering to a patient in need thereof an effective amount of an immunosuppressive agent.

Any immunosuppressive agent may be used according to the invention. Among known immunosuppressive drugs that might be used in the invention are prednisone, methylprednisolone, azathioprine, cyclophosphamide and cyclosporine. In a preferred embodiment, azathioprine is used.

The choice of the immunosuppressive agent, mode of administration, dosage and duration of the treatment will depend on the patient's individual response, his age, and severity of the disease. If necessary, a combination of two different immunosuppressive agents may be used.

BRIEF DESCRIPTION OF THE DRAWINGS

FIGS. 1A–B show 28-week scores of a schizophrenic patient during and after azathioprine treatment, as described in Example 1, wherein FIG. 1A shows scores of level of platelet-associated autoantibodies (PAA) presented in units of optical density (O.D.) per $10^8$ platelets in 1 ml; and FIG. 1B shows scores of psychiatric condition by the positive and negative syndrome scale (PANSS): empty circles—positive syndrome scale; filled circles—negative syndrome scale; empty squares—general psychopathological scale; filled squares, summation of 3 scales.

FIGS. 2A–B show 14-week scores of a schizophrenic patient during and after azathioprine treatment, as described in Example 2, wherein FIG. 2A shows scores of PAA and FIG. 2B shows scores of psychiatric conditions by PANSS, as defined in FIG. 1.

FIGS. 3A–B show 25-week scores of a schizophrenic patient during and after azathioprine treatment, as described in Example 3, wherein FIG. 3A shows scores of PAA and FIG. 3B shows scores of psychiatric conditions by PANSS, as defined in FIG. 1.

DESCRIPTION OF THE INVENTION

Figure 1A:
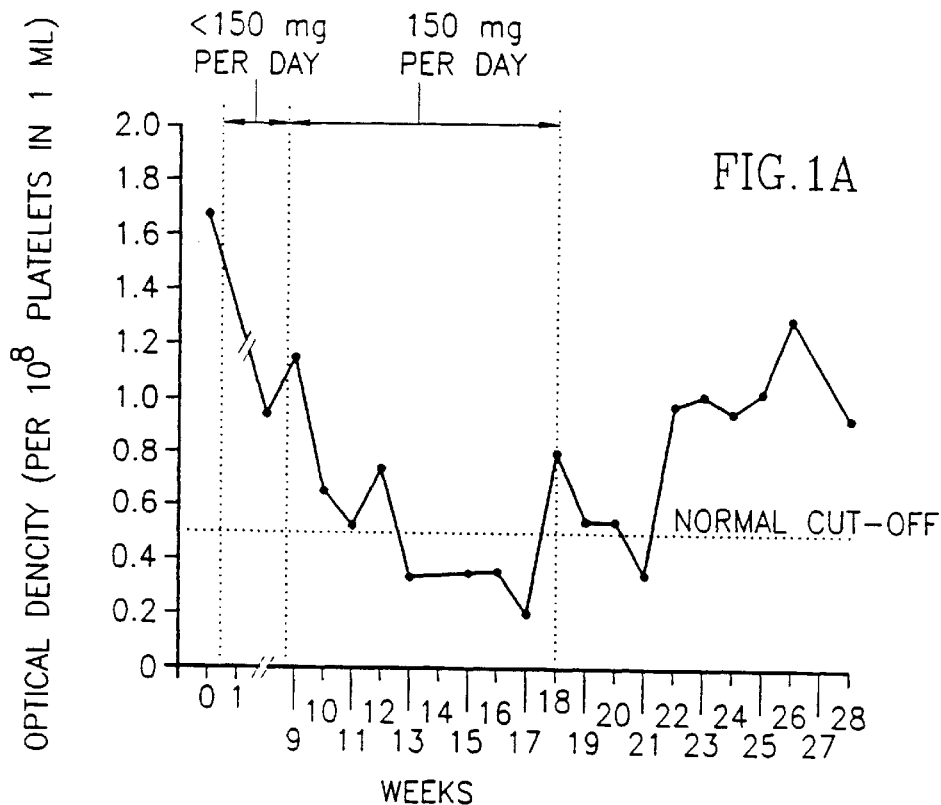

According to the present invention, schizophrenic patients that did not respond to, or showed only limited response to, neuroleptics, were treated with immunosuppressant drugs.

The treatment consisted of three consecutive periods, in which the daily dose of azathioprine first raised from 50 mg to 150 mg, then remained at a constant dose in the second period, and then was gradually tapered and terminated in the third period. The patients remained on treatment with other antipsychotic drugs, such as clothiapine and lithium.

The results of the treatment were followed by the PAA profile and the PANSS psychiatric ratings, as shown in the following non-limiting examples and figures.

EXAMPLES

Example 1

A female patient, V. J., age 52, suffered from paranoid schizophrenia since the age of 25. At the age of 32 she was diagnosed as suffering from systemic lupus erythematosus (SLE), followed by hypothyroidism of unknown etiology. Until the age of 45 she was hospitalized several times due to eruptions of psychotic episodes of paranoid symptomology. She was then diagnosed as suffering from paranoid schizophrenia according to the DSM III verified later by the DSM III-R. Since the age of 46 she is permanently hospitalized in a Psychiatric Hospital. She had frequent psychotic episodes, manifested by bizarre paranoid thoughts accompanied by command hallucinations, extreme psychomotor agitation and total self neglect. Partial apparent remissions lasted for a few weeks only. During the 5 years prior to the present treatment, she was treated with various neuroleptics, lithium and electroconvulsive therapy with only limited response, in addition to prednisone (30 mg/daily) for SLE, and thyroxine (100–150 μg/daily) for hypothyroidism.

A therapeutic regimen with the immune suppressant azathioprine was instituted for the patient, during which her psychiatric condition was assessed by the positive and negative syndrome scale (PANSS) for schizophrenia[9,10]. This scale assesses positive symptoms (delusions, hallucinations etc.) and negative symptoms (blunt affect, emotional withdrawal, etc.) and general psychopathological characteristics. The PANSS has a good inter and intra-rater reliability and has been widely used for psychiatric assessment in various clinical studies[9,10].

The treatment consisted of 3 consecutive periods during which the patient remained on clothiapine (80 mg daily) and lithium (600 mg daily) treatment. In the first (an adjustment of 8 weeks), the chronic steroid treatment (Meticorten, Schering) was gradually tapered from 30 mg/daily to 5 mg/daily, while azathioprine (Imuran™, Borroughs-Wellcome) was given orally starting from 50 mg/daily up to 150 mg/daily. In the second period (10 weeks), azathioprine was administered at a daily dose of 150 mg. During the third period (8 weeks) azathioprine treatment was gradually tapered down to termination. At the beginning of the trial the patient's laboratory values were: Sedimentation rate—35/68; serum immunoglobulins—normal; haemoglobin—11.0 gr/dl; white blood cell count—5600 cmm, with a normal differentiation count and platelet count of 147,000/cmm. Some relevant "autoimmune" parameters were taken shortly before the treatment and 16 weeks after the beginning of the trial (i.e. 8 weeks within the second period). Thus, before treatment, serum C-Reactive Protein (CRP) was 30 mg/dl and rheumatoid factor 200 IU/ml. After treatment, these values returned to normal, while antinuclear factor was reduced from 2+to 1+. At the same time, the platelet count rose from $147 \times 10^9$/L to $260 \times 10^9$/L. These results clearly indicate that the immunosuppressive treatment reduced the production of some autoantibodies and of a major acute phase reactant. The platelet count almost doubled presumably due to a decrease in the titer of platelet-associated autoantibodies, PAA (see below).

At weekly intervals, PAA was assayed on freshly drawn peripheral blood, as previously described[4,6]. A day or two later the PANSS psychiatric rating was performed by a different group uninformed about the PAA values.

The results of the PAA profile and the psychiatric ratings are shown in FIGS. 1A and 13. As shown, the PAA measurement at the beginning of the study (1.55 O.D. units) was over 3-fold higher than the normal cut off level (0.5 O.D. units). Already within the first trial period the PAA value was reduced and in the midst of the second period it reached normal values (FIG. 1A), fluctuating around the cut off level. Four weeks after terminating the azathioprine treatment, the PAA titer was again elevated and approached the initial level (see FIG. 1A).

Figure 1B:
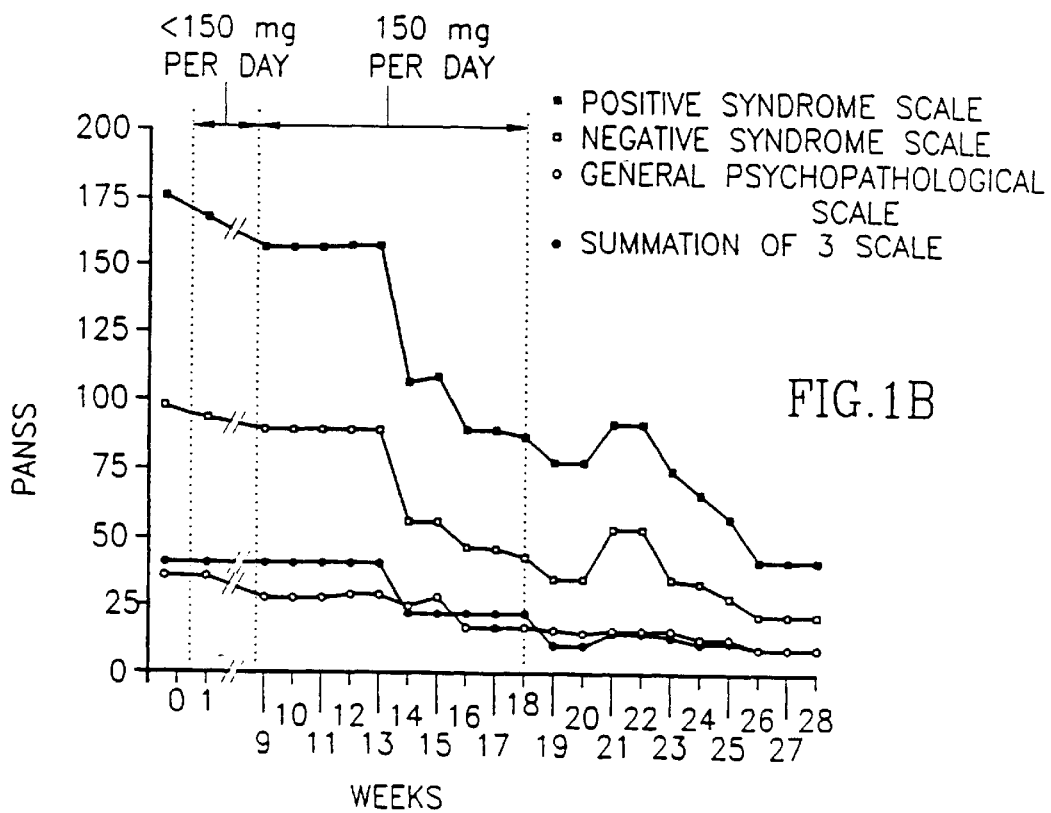

The PANSS scorings at the beginning of the study were typical of a severe psychotic state. A small and probably insignificant reduction in PANSS scoring was noticed at the beginning of the second period of the trial. However, a marked improvement in PANSS scoring was recorded at the 6th week of the second period, which took place approximately one week after the PAA level entered into the normal range (FIGS. 1A and 1B). The psychological improvement of the patient continued well into the third period (FIG. 1B) where the patient was essentially free of treatment. The PANSS ratings indicated a marked psychiatric improvement that followed the decrease in PAA but remained unchanged when the latter relapsed. Today the patient is practically in a state of remission (symptoms below the $25^{th}$ percentile in the PANSS scale) and her appearance and social performance are close to normal.

A broad spectrum of examinations (data not shown) have clearly indicated that the observed effects could neither be attributed to an anti-lupus action of azathioprine, nor to a non-specific steroid effect. It seems plausible, therefore, that in our case immunosuppression induced by azathioprine acted on a putative autoimmune arm of schizophrenia, which was associated with PAA. Along this avenue it might be proposed that after a lag time the action of these autoantibodies in the CNS is subsequently reduced to a level which is overtly manifested in the increase of mental competence (decrease in PANSS score). The ensued reduction in PAA antibodies in the CNS may have either directly alleviated the mental symptomatology or potentiated the therapeutic action of neuroleptics lithium.

The results of this case indicate a possible link between production of PAA and psychotic brain disturbances, and adds to the accumulating evidence that platelets and brain cells have antigenic cross reacting dopaminergic receptors. Based on this notion, and on the results presented here, new directions of research and treatment of mental disorders might be considered.

Example 2

A male patient, S. R., age 51, single, was diagnosed at the age of 24 as suffering from chronic paranoid schizophrenia which was mostly characterized by delusions and violence (physical). The patient did not respond to various neuroleptic treatments. During azathioprine treatment there was a significant improvement of his delusions and physical violence alongside with improved insight to his illness. No adverse effects were recorded.

Figure 2A:
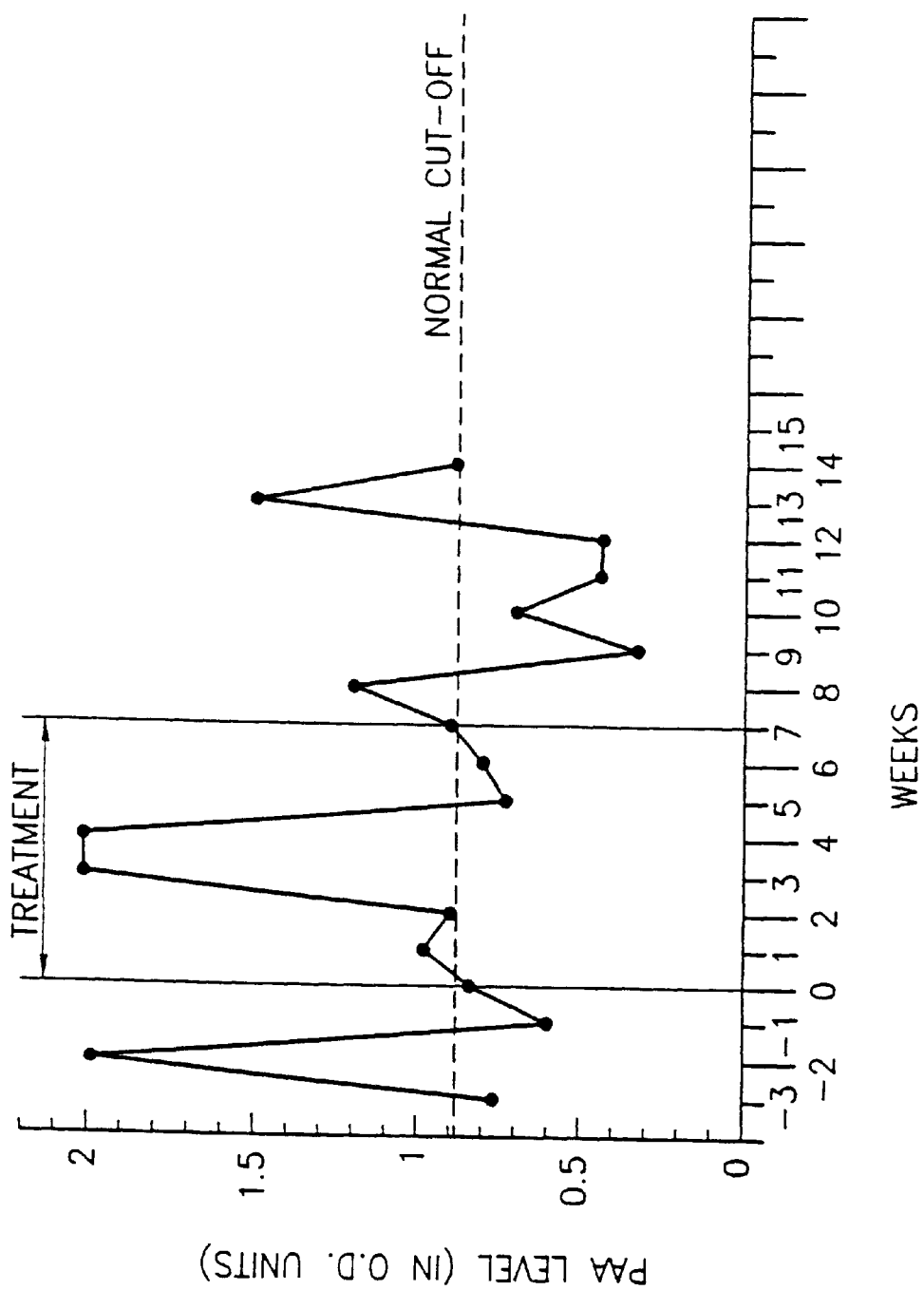
Figure 2B:
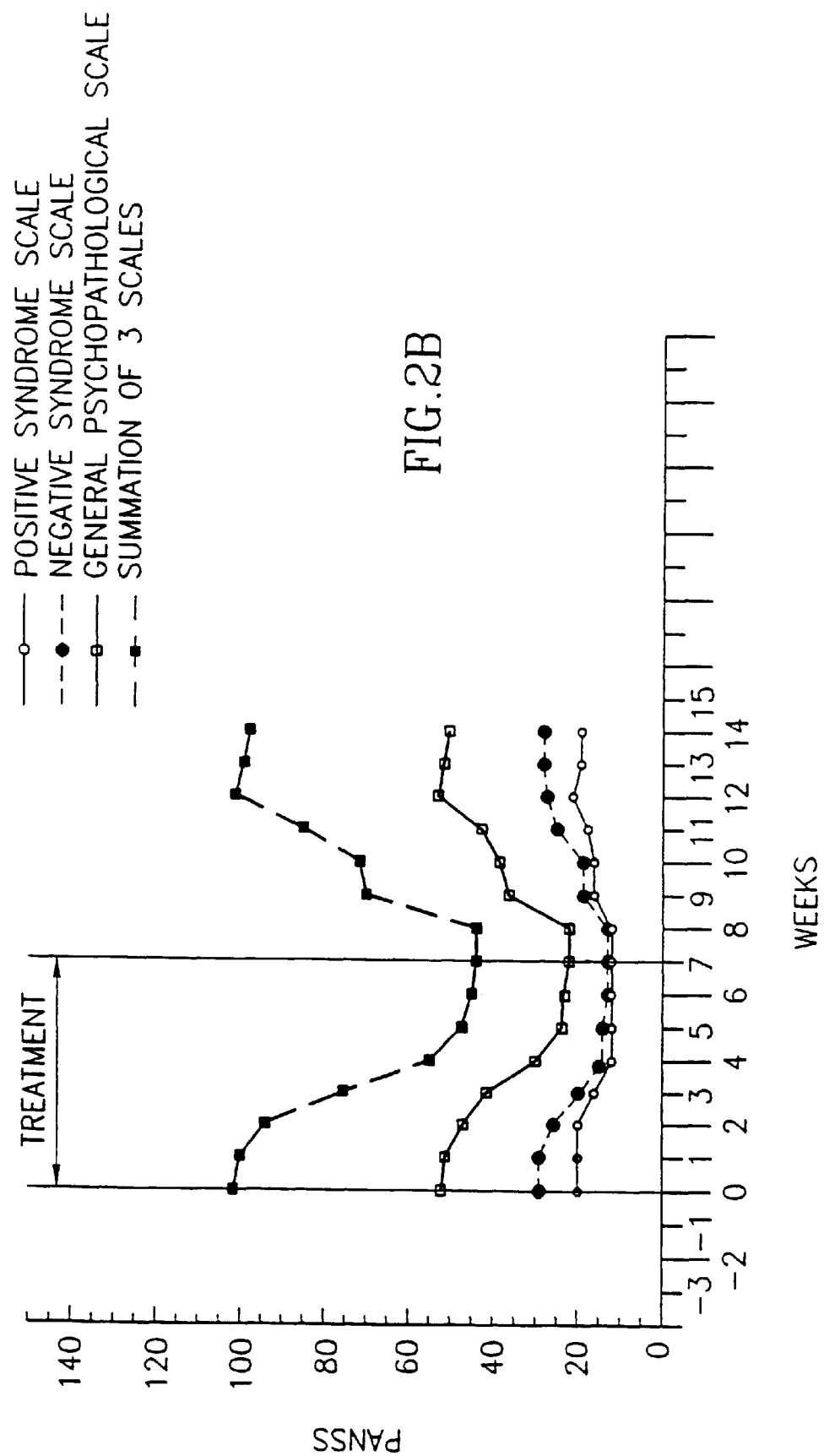

As shown in FIGS. 2A and 25, the PANSS scoring indicated a significant reduction in all parameters (improved psychological rating) in response to the treatment, which relapsed after termination of the treatment. PAA scoring indicated cycling and not much improvement.

Example 3

Figure 3A:
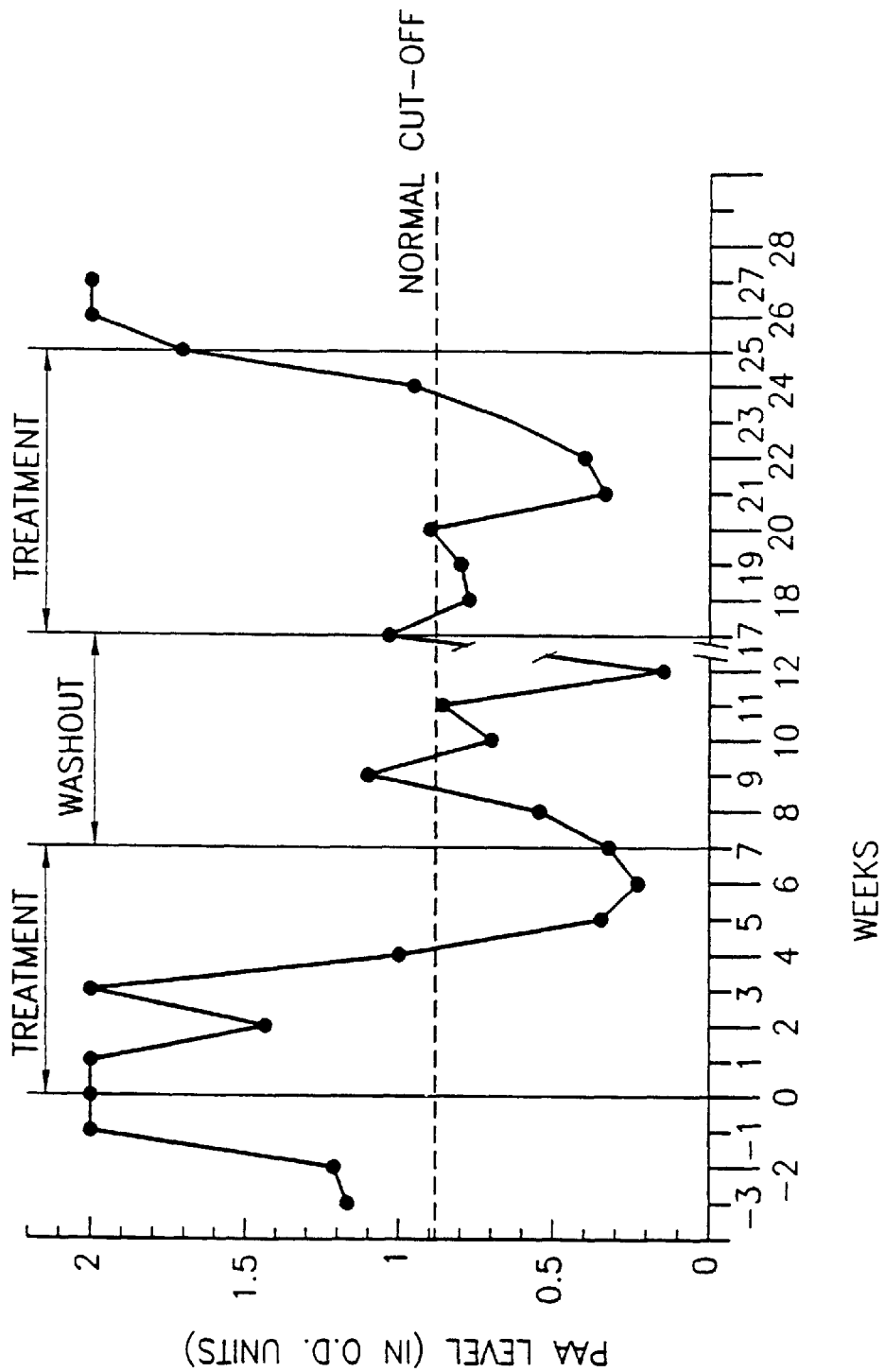
Figure 3B:
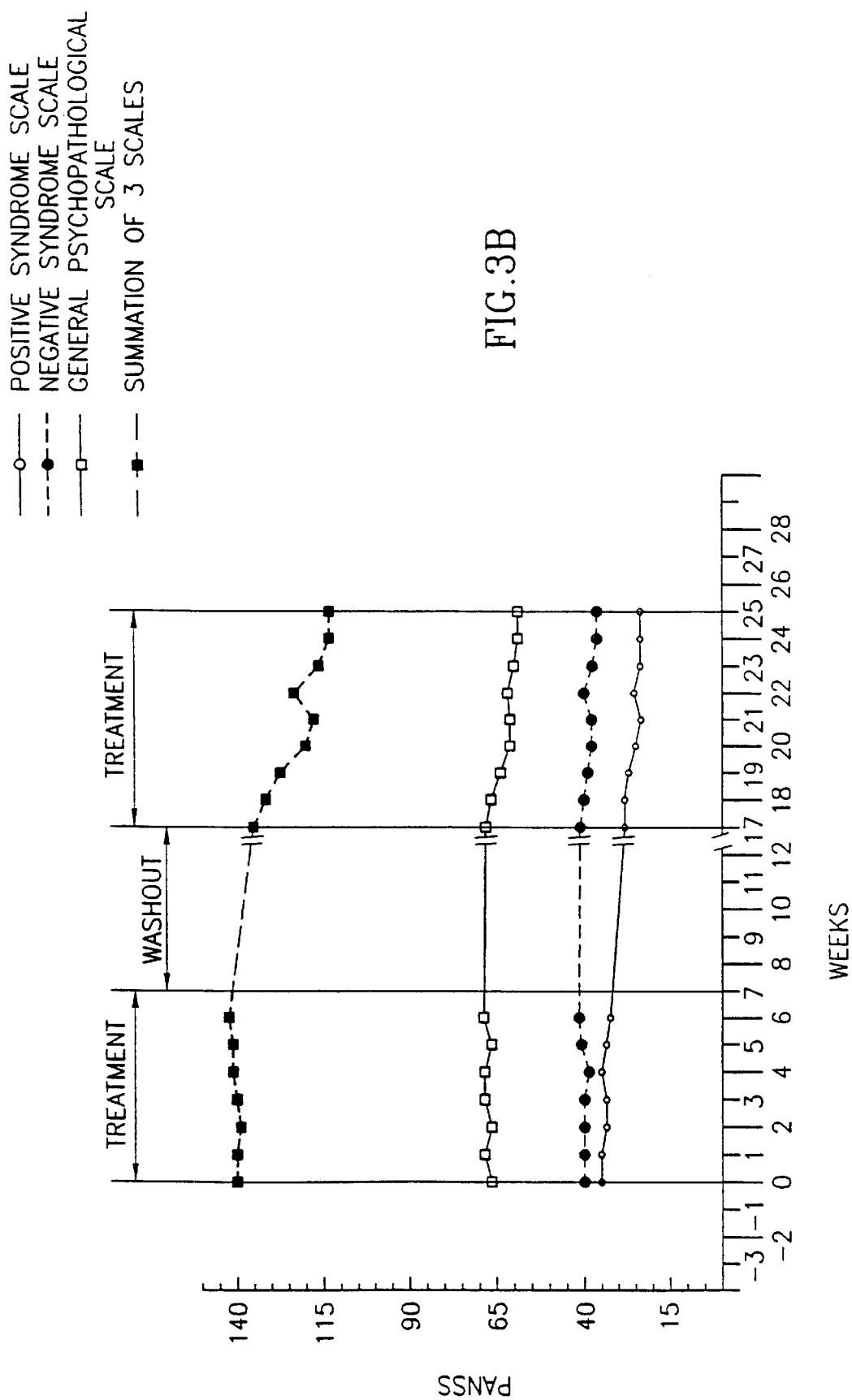

A male patient, P. M., age 41, single, was diagnosed as suffering from chronic paranoid schizophrenia for 23 years, characterized by delusions of reference and persecution and severe violence towards people and property. He did not respond to neuroleptics. There was slight but significant improvement with azathioprine treatment (a significant reduction in PANSS scoring). Blood count and biochemistry remained normal along the trial. PAA titer was normal in the middle of the treatment. The results are shown in FIGS. 3A and 3B.

REFERENCES

1. Knight JG. Is schizophrenia an autoimmune disease? A Review. *Meth. Find. Exp. Clin. Pharmacol.* 1984; 6: 395–402.
2. Jankovic BD. From Immunoneurology to immunopsychiatry. Neuromodulating activity of antibrain antibodies. *Int. Rev. Neurobiol.* 1984; 26: 249–314.
3. DeLisi LE, Weber RJ, Pert CB. Are there antibodies against brain in sera from schizophrenic patients? *Biol. Psychiatry* 1985; 20: 94–119.
4. Shinitzky M., Deckmann M., Kessler A. et al. Platelet autoantibodies in dementia and schizophrenia—possible implication for mental disorders. *Ann. N.Y. Acad. Sci.* 1991; 621: 205–217.
5. Teplizki HA, Sela B, Shoenfeld Y. Autoantibodies to brain and polynucleotides in patients with schizophrenia: a puzzle. *Immunol. Res.* 1992; 11: 66–73.

6. Kessler A, Shinitzky M. Platelets from schizophrenic patients bear autoimmune antibodies which inhibit dopamine uptake. *Psychobiol.* 1993; 21: 299–306.
7. Abramsky O, Litvin Y. Autoimmune response to dopamine-receptor as a possible mechanism in the pathogenesis of Parkinson's disease and schizophrenia. *Perspect. Biol. Med.* 1978; 22: 104–114.
8. Leporrier M, Dighiero G, Auzemery M. Detection and quantification of platelet-bound antibodies with immunoperoxidase. *Br. J. Haematol.* 1979; 42: 605–611.
9. Kay SR, Poler LA, Eiszbein A. Positive and negative syndrome scale (PNASS). Toronto Multi-Heath Systems Inc. (1990).
10. Kay SR. Positive and negative syndromes in schizophrenia; Assessment and research. Bunner and Mazel Publishers, New York, 1991.

We claim:

1. A method of treating schizophrenia in a schizophrenic patient consisting essentially of administering to said patient an effective amount of azathioprine.

2. A method of treating schizophrenia in a schizophrenic patient comprising administering to said patient an effective amount of azathioprine and no antipsychotic drugs.

3. A method of treating schizophrenia in a schizophrenic patient consisting essentially of administering to said patient an effective amount of an immunosuppressive agent.

4. The method according to claim 3, wherein said immunosuppressive agent is selected from the group consisting of prednisone, methylprednisone, azathioprine, cyclophosphamide, and cyclosporine.

5. The method according to claim 4, wherein said immunosuppressive agent is prednisone.

6. The method according to claim 4, wherein said immunosuppressive agent is methylprednisone.

7. The method according to claim 4, wherein said immunosuppressive agent is azathioprine.

8. The method according to claim 4, wherein said immunosuppressive agent is cyclophosphamide.

9. The method according to claim 4, wherein said immunosuppressive agent is cyclosporine.

10. A method of treating schizophrenia in a schizophrenic patient comprising administering to said patient an effective amount of an immunosuppressive agent and no antipsychotic drugs.

11. The method of claim 10, wherein said immunosuppressive agent is prednisone.

12. The method of claim 10, wherein said immunosuppressive agent is methylprednisone.

13. The method of claim 10, wherein said immunosuppressive agent is cyclophosphamide.

14. The method of claim 10, wherein said immunosuppressive agent is cyclosporine.

* * * * *